United States Patent [19]

Koga et al.

[11] Patent Number: 5,646,310
[45] Date of Patent: Jul. 8, 1997

[54] N-(2-CYANOETHYL)-6-FLUOROALKYL-2H-1-BENZOPYRAN DERIVATIVES

[75] Inventors: Hiroshi Koga; Haruhiko Sato; Takenori Ishizawa, all of Shizuoka, Japan

[73] Assignee: Chugai Seiyaku Kabushiki Kaisha, Tokyo, Japan

[21] Appl. No.: 448,576

[22] PCT Filed: Apr. 25, 1994

[86] PCT No.: PCT/JP94/00682

§ 371 Date: Jun. 7, 1995

§ 102(e) Date: Jun. 7, 1995

[87] PCT Pub. No.: WO94/25021

PCT Pub. Date: Nov. 10, 1994

[30] Foreign Application Priority Data

Apr. 23, 1993 [JP] Japan .................... 5-132308
May 7, 1993 [JP] Japan .................... 5-141111

[51] Int. Cl.$^6$ .................... C07D 311/58; A61K 31/35
[52] U.S. Cl. .................................................. 549/405
[58] Field of Search ............................................. 549/405

[56] References Cited

U.S. PATENT DOCUMENTS 5,412,117  5/1995  Koga et al. .................. 549/404

FOREIGN PATENT DOCUMENTS 5-294954  11/1993  Japan .
92/02514   2/1992  WIPO .
92/14439   3/1992  WIPO .

OTHER PUBLICATIONS

Koga et al., CA 118:233885 (1993).
Koga et al., CA 120:106765 (1994).

*Primary Examiner*—Johann Richter
*Assistant Examiner*—Laura L. Stockton
*Attorney, Agent, or Firm*—Browdy and Neimark

[57] ABSTRACT

Described herein are benzopyran derivatives represented by the formula:

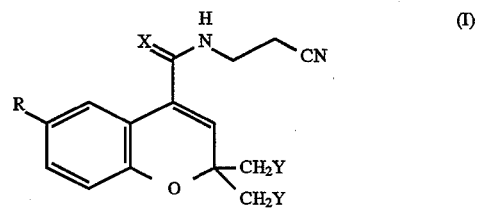

wherein R, X and Y represent any of the following combinations:

| R | X | Y |
|---|---|---|
| $C_2F_5$ | O | H |
| $C_2F_5$ | S | H |
| $CF_3$ | S | F |
| $C_2F_5$ | S | F |
| $C_3F_7$ | S | F | and pharmaceutically acceptable salts thereof. These compounds have an excellent potassium channel activity and are also excellent from the aspect of safety.

6 Claims, No Drawings

N-(2-CYANOETHYL)-6-FLUOROALKYL-2H-1-BENZOPYRAN DERIVATIVES

This application is a 371 of PCT/JP94/00682 filed Apr. 25, 1994.

TECHNICAL FIELD

This invention relates to a benzopyran derivative and a salt thereof which compounds have a strong vasodilating activity as a potassium channel opener and are useful as pharmaceutical agents.

TECHNICAL BACKGROUND

Hitherto, a series of benzopyran derivatives has been known to have various pharmacological activities. For example, Japanese Patent Application (Kokai) Nos. Sho-60-97974, Sho-61-47416, Sho-63-165317, Sho-63-196581, Sho-63-201182, Sho-63-303977, Sho-64-26578, Sho-64-38087 and Hei-2-129184, and Journal of Medicinal Chemistry, Vol. 33, No. 6, pages 1529–1541, 1990, etc. disclose various benzopyran derivatives in which the carbon atom at the 4-position of the benzopyran ring is directly bonded to a nitrogen atom, and these compounds have been described as having an antihypertensive activity and being usable for the treatment of cardiac disorders, etc.

Further, Japanese Patent Application (Kokai) Nos. Sho-63-303977 and Sho-64-38087, WO 90/14346 and WO 92/14439, Journal of Heterocyclic Chemistry, Vol. 11, No. 5, pages 797–802, 1974, etc. disclose benzopyran derivatives in which the carbon atom at the 4-position of the benzopyran ring is not directly bonded to a nitrogen atom.

WO 90/14346 and WO 92/14439 disclose compounds having a general formula which includes, within its scope, a part of the compounds of the present invention wherein the 4-position of the benzopyran ring is substituted with an amido group or a thioamido group. Further, WO 92/14439 discloses compounds of the general formula which includes, within its scope, the compounds of the present invention and describes that these compounds are useful as a trichogenous agent. More specifically, WO 92/14439 discloses the compounds which include the compounds of the present invention and which are represented by the general formula:

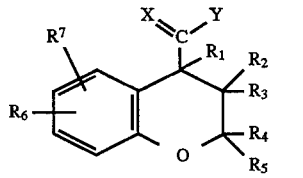

(II)

wherein X represents =O, =S, =N—Z or =CHNO$_2$, in which Z represents a hydrogen atom, a lower alkyl group, an aryl group, a hydroxy group, a lower alkoxy group, a cyano group, a carbamoyl group or a sulfamoyl group; Y represents —NR$_8$R$_9$, —OR$_{10}$ or —SR$_{11}$, in which R$_8$ and R$_9$ may be the same or different and each represents a hydrogen atom, a hydroxy group, a lower alkoxy group, a cyano group, an amino group which may have (a) substituents, a lower alkyl group which may have (a) substituents, an unsaturated lower alkyl group which may have (a) substituents, a cycloalkyl group which may have (a) substituents, an aryl group which may have (a) substituents, a heteroaryl group which may have (a) substituents, or, when taken together with the nitrogen atom, R$_8$ and R$_9$ jointly represent a heterocyclic group which may have (a) substituents, R$_{10}$ and R$_{11}$ each represents a hydrogen atom, a lower alkyl group or an aryl group; R$_1$ represents a hydrogen atom, a lower alkyl group or an aryl group, or forms a single bond when bonded directly to R$_2$, R$_2$ and R$_3$ may be the same or different and each represents a hydrogen atom or a hydroxy group, or, when taken together, form =O; R$_4$ and R$_5$ may be the same or different and each represents a hydrogen atom or a lower alkyl group which may have (a) substituents, or, when taken together, represent a polymethylene group; R$_6$ and R$_7$ may be the same or different and each represents a hydrogen atom, a lower alkyl group, a lower haloalkyl group, a halogen atom, a lower alkoxy group, a lower haloalkoxy group an amino group, an acylamino group, a nitro group, a cyano group, an ester group, a lower alkylsulfonyl group or an arylsulfonyl group, or, when taken together, represent =N—O—N=. However, this publication does not specifically describe the structure and the name of the compounds of the present invention and further does not suggest at all that the compounds of the present invention exhibit an unexpectedly remarkable effect as a potassium channel opener.

In these conventional compounds, cromakalim is now developed as a new type of hypotensive agents, but the activity thereof is still unsatisfactory. Also, some other compounds have an activity higher than that of cromakalim, but many of them have problems from the aspect of safety since they exhibit disturbance of organs such as the lungs and have a property of mutagenicity.

As a result of extensive studies by the present inventors with respect of compounds having a potassium channel activity higher than that of the conventional closely-related compounds including a typical cromakalim and having fewer problems from the aspect of safety, the present inventors found that the compounds of the present invention solve the conventional problems and exhibit an excellent effect as a pharmaceutical agent and completed the present invention.

DISCLOSURE OF THE INVENTION

The compound of the present invention is a benzopyran derivative represented by the general formula:

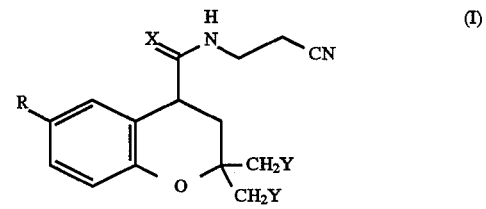

(I)

wherein R, X and Y represent any of the following combinations:

| R | X | Y |
|---|---|---|
| C$_2$F$_5$ | O | H |
| C$_2$F$_5$ | S | H |
| CF$_3$ | S | F |
| C$_2$F$_5$ | S | F |
| C$_3$F$_7$ | S | F | and a pharmaceutically acceptable salt thereof.

These compounds of the present invention are novel compounds which have not been specifically disclosed in literature references, have an excellent potassium channel activity and are useful as pharmaceutical agents such as an antihypertensive agent, etc.

The compound of the present invention can be prepared, for example, in the following manner.

The compound can be obtained by reacting a compound represented by the general formula:

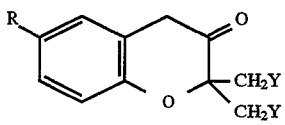

wherein R and Y are as defined above, with a compound represented by the general formula:

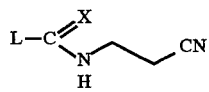

wherein L represents a releasing group such as a halogen atom, —OR₁, —S(O)nR₂, etc., and X is as defined above, in the presence of a base in an inert solvent, followed by conducting reduction and dehydration reactions.

Examples of the base which can be used include sodium hydride, a sodium alkoxide, a potassium alkoxide, an alkyl lithium, potassium carbonate, sodium carbonate, potassium hydroxide and sodium hydroxide.

Also, the compound of the present invention can be obtained by reacting the compound of the above formula (III) with a compound represented by the general formula (V):

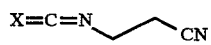

wherein X is as defined above, in place of the compound of the general formula (IV), and then conducting the same treatments.

Alternatively, the compound of the present invention wherein X is a sulfur atom can be obtained by reacting a compound represented by the general formula:

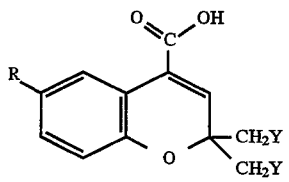

wherein R and Y are as defined above with 2-cyanoethylamine in an inert solvent using an appropriate condensing agent, which is produced by reacting a compound represented by the general formula:

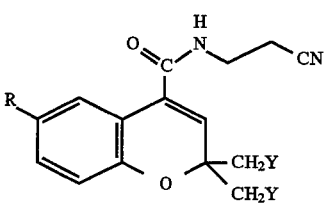

wherein R and Y are as defined above, with a Lawesson's reagent or phosphorus pentasulfide.

Examples of the condensing agent which can be used include N,N'-carbonyldiimidazole and triphenylphosphine, and an amidation reagent such as 2,2'-dipyridylsulfide.

The compound of the present invention exhibits an excellent potassium channel activity equivalent to or higher than the conventional benzopyran type compound, typically, cromakalim, and can be used as an active component of a potassium channel opener such as a smooth muscle relaxant, that is, an anti-asthmatic agent, an anti-hypertensive agent, anti-angina pectoris agent and a treating agent for urine incontinence.

Also, from the aspect of safety which is an important factor in pharmaceutical agents, the compound of the present invention has a high safety without exhibiting disturbance on organs such as lung and antigenicity which are observed in the conventional compounds.

The dosage level of the compound according to the present invention varies depending upon the type and severity of the diseases and the patient, but is generally in the range of from 0.0001 to 1 mg/kg/day, preferably from 0.001 to 0.1 mg/kg/day. The route of administration can be selected from oral administration, parenteral administration and topical administration according to the necessity.

The preparation of the compound of the present invention is further illustrated with reference to the following examples, but the present invention is not limited by these examples.

EXAMPLE 1

Synthesis of N-(2-cyanoethyl)-6-pentafluoroethyl-2,2-dimethyl-2H-1-benzopyran-4-carbamide (Compound 1)

1.1 g of tertiary-butoxy potassium and 2 ml of a dimethylformamide solution of 2 g of 2-cyanoethyl isothiocyanate were subsequently added to a mixture of 2.6 g of 6-pentafluoroethyl-3,4-dihydro-2,2-dimethyl-2H-1-benzopyran-3-one and 28 ml of dimethylformamide while stirring at −5° C., followed by stirring at 5° C. for 15 hours. Then, 2N hydrochloric acid was added thereto, and the mixture was extracted with ether. After washing the organic layer with water and drying, the residue obtained by distilling off the solvent was purified by silica gel column chromatography (a developing solution, hexane:methylene chloride=1:2) to obtain 2.6 g of N-(2-cyanoethyl)-6-pentafluoroethyl-3-hydroxy-2,2-dimethyl-2H-1-benzopyran-4-carbamide. 2.1 g of sodium cyanoborohydride was added to a mixture of 2.6 g of N-(2-cyanoethyl)-6-pentafluoroethyl-3-hydroxy-2,2-dimethyl-2H-1-benzopyran-4-carbamide obtained above, 15 ml of acetic acid and 45 ml of tetrahydrofuran while ice-cooling and stirring, and the resulting mixture was stirred at room temperature for 13 hours. The mixture was diluted with ethyl acetate, and, after washing the organic layer with a saturated aqueous solution of sodium bicarbonate and water and drying, the solvent was distilled off to obtain 2.6 g of N-(2-cyanoethyl)-6-pentafluoroethyl-3,4-dihydro-3-hydroxy-2,2-dimethyl-2H-1-benzopyran-4-carbamide. Then, the product was added to 90 ml of pyridine and 3.4 g of tosyl chloride, and the mixture was heated while refluxing for 1 hour. After concentration under reduced pressure, water and concentrated hydrochloric acid were added thereto, followed by extracting with methylene chloride. After washing the organic layer with water and drying, the residue obtained by distilling off the solvent was purified by silica gel column chromatography (a developing solution, hexane:ethyl acetate=1:1) to obtain 460 mg of N-(2-cyanoethyl)-6-pentafluoroethyl-2,2-dimethyl-2H-1-benzopyran-4-carbamide having a melting point of 163°–164° C.

NMR (CDCl₃, δ): 1.49 (6H,s), 2.71 (2H,t), 3.64 (2H,q), 6.04 (1H,s), 6.20–6.52 (1H,m), 6.85 (1H,d), 7.36 (1H,dd), 7.74 (1H,d)

MS mz: 374 (M⁺)

EXAMPLE 2

Synthesis of N-(2-cyanoethyl)-6-pentafluoroethyl-2,2-dimethyl-2H-1-benzopyran-4-carbothioamide (Compound 2)

227 mg of Lawesson's reagent was added to a mixture of 210 mg of N-(2-cyanoethyl)-6-pentafluoroethyl-2,2- dimethyl-2H-1-benzopyran-4-carbamide obtained according to Example 1 and 20 ml of benzene, and the resulting mixture was heated while refluxing for 1 hour. After concentrating the mixture under reduced pressure, the resulting residue was purified by silica gel column chromatography (a developing solution: methylene chloride) to obtain 180 mg of N-(2-cyanoethyl)-6-pentafluoroethyl-2,2-dimethyl-2H-1-benzopyran-4-carbothioamide.

NMR (CDCl$_3$, δ): 1.48 (6H,s), 2.84 (2H,t), 3.96 (2H,q), 5.83 (1H,s), 6.83 (1H,d), 7.32 (1H,dd), 7.53 (1H,d), 7.79–8.21 (1H,m)

MS mz: 390 (M$^+$)

EXAMPLE 3

Synthesis of N-(2-cyanoethyl)-2,2-bisfluoromethyl-6-tri-fluoromethyl-2H-1-benzopyran-4-carbothioamide (Compound 3)

(1) 2.52 ml of trimethylsilylcyanide and 0.82 g of zinc iodide were added to a mixture of 4.05 g of 2,2-bisfluoromethyl-3,4-dihydro-6-nitro-2H-1-benzopyran-4-one and 10 ml of dried benzene, and the mixture was stirred at room temperature for 12 hours. Further, 8 ml of pyridine and 4.41 ml of phosphorus oxychloride were added thereto, followed by heat-refluxing for 6 hours. Ice water was added to the reaction mixture which was then made acidic with hydrochloric acid, and the mixture was extracted with methylene chloride. After washing the organic layer with water and drying, the residue obtained by concentration under reduced pressure was subjected to silica gel column chromatography (an eluting solvent: methylene chloride:hexane=7:3) to obtain 0.99 g of 2,2-bisfluoromethyl-6-nitro-2H-1-benzopyran-4-carbonitrile having a melting point of 136°–137° C.

H$^1$-NMR (CDCl$_3$, δ): 4.59 (4H,d), 6.53 (1H,s), 7.03 (1H,d), 8.10–8.40 (2H,m)

MS: 266 (M$^+$)

(2) A mixture of 0.93 g of 2,2-bisfluoromethyl-6-nitro-2H-1-benzopyran-4-carbonitrile, 20 ml of acetic acid, 10 ml of water and 10 ml of sulfuric acid was heated while refluxing for 4.5 hours. The reaction mixture was poured into ice-water, and the precipitated crystals were separated by filtration to obtain 0.83 g of 2,2-bisfluoromethyl-6-nitro-2H-1-benzopyran-4-carboxylic acid having a melting point of 171°–172° C.

IR (KBr) cm$^{-1}$=1698 (C=O)

MS: 285 (M$^+$)

(3) A mixture of 41.7 of 2,2-bisfluoromethyl-6-nitro-2H-1-benzopyran-4-carboxylic acid, 20 ml of sulfuric acid and 300 ml of ethyl alcohol was heated under refluxing for 6 hours. The reaction mixture was poured into ice-water, and the precipitated crystals were separated by filtration to obtain 42.7 g of ethyl 2,2-bisfluoromethyl-6-nitro-2H-1-benzopyran-4-carboxylate having a melting point of 96°–98° C.

H$^1$-NMR (CDCl$_3$, δ): 1.42 (3H,t), 4.38 (2H,q), 4.58 (4H,d), 6.69 (1H,s), 6.94 (1H,d), 8.07 (1H,dd), 8.92 (1H,d)

MS: 313 (M$^+$)

(4) A mixture of 42.0 g of ethyl 2,2-bisfluoromethyl-6-nitro-2H-1-benzopyran-4-carboxylate, 88 g of stannous chloride and 500 ml of ethyl alcohol was heated while refluxing for 2 hours. A 2N aqueous solution of sodium hydroxide was added to the reaction mixture, followed by extracting with ethyl acetate. The organic layer was washed with brine, dried over sodium sulfate and then concentrated under reduced pressure to obtain 5,2 g of ethyl 6-amino-2,2-bisfluoromethyl-2H-1-benzopyran-4-carboxylate as an oily substance.

H$^1$-NMR (CDCl$_3$, δ): 1.31 (3H,t), 3.0–4.0 (2H,m), 4.36 (2H,q), 4.55 (4H,d), 6.2–6.9 (⊖H,m), 7.26 (1H,d)

MS: 283 (M$^+$)

(5) A mixture of 1.09 g of sodium nitrite, 10 ml of methylene chloride and 10 ml of water was added to a mixture of 4.0 g of ethyl 6-amino-2,2-bisfluoromethyl-2H-1-benzopyran-4-carboxylate, 1.66 g of sulfuric acid and 40 ml of water under ice cooling, followed by stirring under ice cooling for 10 minutes. Further, a mixture of 2.85 g of potassium iodide and 5 ml of water was added to the reaction mixture, followed by stirring at room temperature for 1.5 hour. Water was added to the reaction mixture, and the mixture was extracted with methylene chloride. The organic layer was washed with a 20% aqueous solution of sodium sulfite and a brine and then dried over sodium sulfate. The residue obtained by concentration under reduced pressure was subjected to silica gel column chromatography (an eluting solvent, ethyl acetate:hexane=1:1) to obtain 3.67 g of ethyl 2,2-bisfluoromethyl-6-iodo-2H-1-benzopyran-4-carboxylate having a melting point of 89°–90° C.

H$^1$-NMR (CDCl$_3$, δ): 1.39 (3H,t), 4.33 (2H,q), 4.58 (4H,d), 6.60 (1H,s), 6.67 (1H,d), 7.02 (1H,dd), 8.30 (1H,d)

MS: 394 (M$^+$)

(6) A mixture of 1.00 g of ethyl 2,2-bisfluoromethyl-6-iodo-2H-1-benzopyran-4-carboxylate, 0.84 g of potassium trifluoroacetate, 1.18 g of cuprous iodide, 4 ml of toluene and 10 ml of N,N-dimethylformamide was heated with stirring at 150° C. for 5.5 hours in a nitrogen gas atmosphere while removing toluene. The reaction mixture was added to a mixed solution of 2N hydrochloric acid and ethyl acetate, and an insoluble material was separated by filtration using celite. The organic layer was separated from the filtrate, and the aqueous layer was extracted with ethyl acetate. The resulting organic layers were combined, washed with a brine, dried over sodium sulfate and concentrated under reduced pressure. The resulting residue was subjected to silica gel column chromatography (an eluting solvent, ethyl acetate:hexane =10:1) to obtain 0.51 g of ethyl 2,2-bisfluoromethyl-6-trifluoromethyl-2H-1-benzopyran-4-carboxylate as an oily substance.

H$^1$-NMR (CDCl$_3$, δ): 1.36 (3H,t), 4.31 (2H,q), 4.53 (4H,d), 6.63 (1H,s), 6.94 (1H,d), 7.47 (1H,dd), 8.31 (1H,d)

MS: 336 (M$^+$)

(7) A mixture of 0.51 g of ethyl 2,2-bisfluoromethyl-6-trifluoromethyl-2H-1-benzopyran-4-carboxylate, 0.13 g of potassium hydroxide and 10 ml of ethyl alcohol was stirred at room temperature for 2 hours. Ice water and hydrochloric acid were added to the reaction mixture, and the precipitated crystals were separated by filtration to obtain 0.43 g of 2,2-bisfluoromethyl-6-trifluoromethyl-2H-1-benzopyran-4-carboxylic acid.

H$^1$-NMR (CDCl$_3$, δ): 4.60 (4H,d), 6.69 (1H,s), 7.00 (1H,d), 7.45 (1H,dd), 8.30 (1H,d)

MS: 308 (M$^+$)

(8) A mixture of 2,2-bisfluoromethyl-6-trifluoro-methyl-2H-1-benzopyran-4-carboxylic acid, 0.12 g of N,N'-carbonyldiimidazole and 3 ml of tetrahydrofuran was stirred at room temperature for 1 hour. 0.06 g of 2-cyanoethylamine was added to the reaction mixture, and the mixture was further stirred at room temperature for 14 hours. The reaction mixture was concentrated under reduced pressure, and the resulting residue was subjected to silica gel column chromatography (an eluting solvent, ethyl acetate:hexane= 1:1) to obtain 0.20 g of N-(2-cyanoethyl)-2,2-bisfluoromethyl-6-trifluoromethyl-2H-1-benzopyran-4-carbamide having a melting point of 135°–136° C.

$H^1$-NMR (CDCl$_3$, δ): 2.70 (2H,t), 3.63 (2H,q), 4.57 (4H,d), 6.08 (1H,s), 6.5–7.3 (1H,m), 6.98 (1H,d), 7.50 (1H,dd), 7.84 (1H,d)

MS: 360 (M$^+$)

(9) A mixture of 92 mg of N-(2-cyanoethyl)-2,2-bisfluoromethyl-6-trifluoromethyl-2H-1-benzopyran-4-carbamide, 60 mg of Lawesson's reagent and 2 ml of benzene was heated while stirring at 80° C. for 1 hour. The reaction mixture was subjected to silica gel chromatography (an eluting solvent: methylene chloride) to obtain 50 mg of N-(2-cyanoethyl)-2,2-bisfluoromethyl-6-trifluoromethyl-2H-1-benzopyran-4-carbothioamide having a melting point of 105°–106° C.

$H^1$-NMR (CDCl$_3$, δ): 2.89 (t, 2H), 4.03 (q,2H), 4.60 (d,4H), 5.87 (s,1H), 7.02 (d,1H), 7.51 (dd, 1H), 7.82 (d, 1H), 8.10–8.70 (brs,1H)

MS: 376 (M$^+$)

EXAMPLE 4

Synthesis of N-(2-cyanoethyl)-6-pentafluoroethyl-2,2-bis-fluoromethyl-2H-1-benzopyran-4-carbothioamide (Compound 4)

(1) In the same manner as described in Example 3 (6) but using ethyl 2,2-bisfluoromethyl-6-iodo-2H-1-benzopyran-4-carboxylate, potassium pentafluoropropionate, cuprous iodide, toluene and N,N-dimethylformamide, ethyl 6-pentafluoroethyl-2,2-bisfluoromethyl-2H-1-benzopyran-4-carboxylate was obtained as an oily substance.

$H^1$-NMR (CDCl$_3$, δ): 1.40 (3H,t), 4.38 (2H,q), 4.60 (4H,d), 6.69 (1H,s), 7.00 (1H,d), 7.45 (1H,dd), 8.30 (1H,d)

MS: 386 (M$^+$)

(2) In the same manner as described in Example 3 (7) but using ethyl 6-pentafluoroethyl-2,2-bisfluoromethyl-2H-1-benzopyran-4-carboxylate, 6-pentafluoroethyl-2,2-bisfluoromethyl-2H-1-benzopyran-4-carboxylic acid having a melting point of 173°–174° C. was obtained.

$H^1$-NMR (CDCl$_3$, δ): 4.60 (2H,d), 6.69 (1H,s), 7.00 (1H,d), 7.45 (1H,dd), 8.30 (1H,d)

MS: 358 (M$^+$)

(3) In the same manner as described in Example 3 (8) but using 6-pentafluoroethyl-2,2-bisfluoromethyl-2H-1-benzopyran-4-carboxylic acid, N-(2-cyanoethyl)-6-pentafluoroethyl-2,2-bisfluoromethyl-2H-1-benzopyran-4-carbamide having a melting point of 144°–145° C. was obtained.

$H^1$-NMR (CDCl$_3$, δ): 2.72 (2H,t), 3.65 (2H,q), 4.60 (4H,d), 6.09 (1H,s), 6.5–7.3 (1H,m), 7.02 (1H,d), 7.52 (1H,dd), 7.83 (1H,d)

MS: 410 (M$^+$)

(4) In the same manner as described in Example 3 (9) but using N-(2-cyanoethyl)-6-pentafluoroethyl-2,2-bisfluoromethyl-2H-1-benzopyran-4-carbamide, N-(2-cyanoethyl)-6-pentafluoroethyl-2,2-bisfluoromethyl-4-carbamide having a melting point of 108°–109° C. was obtained.

$H^1$-NMR (CDCl$_3$, δ): 2.89 (2H,t), 4.04 (2H,q), 4.57 (4H,d), 5.84 (1H,s), 7.00 (1H,d), 7.46 (1H,dd), 7.64 (1H,d), 7.90–8.40 (brs,1H)

MS: 426 (M$^+$)

EXAMPLE 5

Synthesis of N-(2-cyanoethyl)-2,2-bisfluoromethyl-6-heptafluoropropyl-2H-1-benzopyran-4-carbothioamide (Compound 5)

(1) In the same manner as described in Example 3 (6) but using ethyl 2,2-bisfluoromethyl-6-iodo-2H-1-benzopyran-4-carboxylate, potassium heptafluorobutylate, cuprous iodide, toluene and N,N-dimethylformamide, ethyl 2,2-bisfluoromethyl-6-heptafluoropropyl-2H-1-benzopyran-4-carboxylate was obtained as an oily substance.

$H^1$-NMR (CDCl$_3$, δ): 1.36 (3H,t), 4.32 (2H,q), 4.57 (4H,d), 6.69 (1H,s), 7.02 (1H,d), 7.46 (1H,dd), 8.29 (1H,d)

MS: 436 (M$^+$)

(2) In the same manner as described in Example 3 (7) but using ethyl 2,2-bisfluoromethyl-6-heptafluoropropyl-2H-1-benzopyran-4-carboxylate, 2,2-bisfluoromethyl-6-heptafluoropropyl-2H-1-benzopyran-4-carboxylic acid having a melting point of 162°–163° C. was obtained.

$H^1$-NMR (CDCl$_3$, δ): 4.60 (4H,d), 6.69 (1H,s), 7.00 (1H,d), 7.45 (1H,dd), 8.30 (1H,d)

MS: 408 (M$^+$)

(3) In the same manner as described in Example 3 (8) but using 2,2-bisfluoromethyl-6-heptafluoropropyl-2H-1-benzopyran-4-carboxylic acid, N-(2-cyanoethyl)-2,2-bisfluoromethyl-6-heptafluoropropyl-2H-1-benzopyran-4-carbamide having a melting point of 135°–136° C. was obtained.

$H^1$-NMR (CDCl$_3$, δ): 2.70 (2H,t), 3.62 (2H,q), 4.58 (4H,d), 6.05 (1H,s), 6.5–7.3 (1H,m), 6.98 (1H,d), 7.43 (1H,dd), 7.78 (1H,d)

MS: 460 (M$^+$)

(4) In the same manner as described in Example 3 (9) but using N-(2-cyanoethyl)-1,2-bisfluoromethyl-6-heptafluoropropyl-2H-1-benzopyran-4-carbamide, N-(2-cyanoethyl)-2,2-bisfluoromethyl-6-heptafluoropropyl-2H-1-benzopyran-4-carbothioamide having a melting point of 94°–95° C. was obtained.

$H^1$-NMR (CDCl$_3$, δ): 2.85 (2H,t), 3.95 (2H,q), 4.51 (4H,d), 5.78 (1H,s), 6.92 (1H,d), 7.47 (1H,dd), 7.56 (1H,d), 7.90–8.40 (brs,1H)

MS: 476(M$^+$)

TEST EXAMPLE 1

Test Method Using Extracted Rat Aorta

A thoracic aorta was extracted from male Sprague Dawley rat (450–600 g) to prepare a ring-formed sample having a width of 2 mm. The resulting sample was suspended at a tension of 2 g in an organ bath containing Krebs-Henseleit solution, and a gas composed of 95% oxygen and 5% carbon dioxide was passed therethrough. A constriction reaction of the sample was recorded isometrically by a FD pick-up. After equilibration for 1 to 1.5 hour, 30 mM potassium chloride was added in order to constrict the tissue, and an activity of the test compound for relaxing the continuous constriction caused by potassium chloride was evaluated by determining a 50% inhibitory concentration (IC$_{50}$). As comparative compounds, N-(2-cyanoethyl)-2,2-dimethyl-6-nitro-2H-1-benzopyran-4-carbamide (Compound A) disclosed in WO 92/02514 and 6-trifluoromethyl—N-methyl-2,2-dimethyl-2H-1-benzopyran-4-carbothioamide (Compound B) disclosed in WO 92/14439 were used. The results are shown in Table below.

| Test Compound | IC$_{50}$ (M) |
| --- | --- |
| Compound A | 2.8 × 10$^{-9}$ |
| Compound B | 1.9 × 10$^{-9}$ |

-continued

| Test Compound | IC$_{50}$ (M) |
|---|---|
| Compound 1 | $2.4 \times 10^{-10}$ |
| Compound 2 | $8.8 \times 10^{-10}$ |

TEST EXAMPLE 2

Test Method Using Extracted Rat Aorta

A thoracic aorta was extracted from male Sprague Dawley rat (450–600 g) to prepare a ring-formed sample having a width of 2 mm. The resulting sample was suspended at a tension of 2 g in a 2 ml organ bath containing Krebs-Henseleit solution, and a gas composed of 95% oxygen and 5% carbon dioxide was passed therethrough. A constriction reaction of the sample was recorded isometrically by a FD pick-up. After equilibration for 1 to 1.5 hour, 30 mM potassium chloride was added in order to constrict the tissue, and an activity of the test compound for relaxing the continuous constriction caused by potassium chloride was evaluated by determining a 50% inhibitory concentration (EC$_{50}$) of the compound relative to the maximum relaxation effect of the compound. The results are shown in Table below.

| Test Compound | EC$_{50}$ (μM) |
|---|---|
| Compound 3 | 0.000021 |
| Compound 4 | 0.000019 |
| Cromakalim | 0.17 |

We claim:
1. A benzopyran derivative represented by the formula:

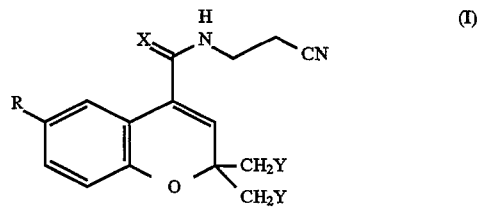

wherein R, X and Y represent any of the following combinations:

| R | X | Y |
|---|---|---|
| C$_2$F$_5$ | O | H |
| C$_2$F$_5$ | S | H |
| CF$_3$ | S | F |
| C$_2$F$_5$ | S | F |
| C$_3$F$_7$ | S | F | or and a pharmaceutically acceptable salt thereof.

2. N-(2-cyanoethyl)-6-pentafluoroethyl-2,2-dimethyl-2H-1-benzopyran-4-carbamide.

3. N-(2-cyanoethyl)-6-pentafluoroethyl-2,2-dimethyl-2H-1-benzopyran-4-carbothioamide.

4. N-(2-cyanoethyl)-2,2-bisfluoromethyl-6-trifluoromethyl-2H-1-benzopyran-4-carbothioamide.

5. N-(2-cyanoethyl)-6-pentafluoroethyl-2,2-bisfluoromethyl-2H-1-benzopyran-4-carbothioamide.

6. N-(2-cyanoethyl)-2,2-bisfluoromethyl-6-heptafluoropropyl-2H-1-benzopyran-4-carbothioamide.

* * * * *